United States Patent [19]

Ninomiya et al.

[11] Patent Number: 4,605,857

[45] Date of Patent: Aug. 12, 1986

[54] TENSILE TESTER

[75] Inventors: Sunao Ninomiya, Ichihara; Yasuhiro Miura, Chiba; Hiromu Iwata, Kisarazu; Shuji Matsuyama, Ichihara, all of Japan

[73] Assignee: Sumitomo Chemical Company, Ltd., Osaka, Japan

[21] Appl. No.: 618,607

[22] Filed: Jun. 8, 1984

[30] Foreign Application Priority Data

Jun. 20, 1983 [JP] Japan .................................. 58-110535

[51] Int. Cl.⁴ .......................... G01T 1/22; G01T 1/24
[52] U.S. Cl. .................................... 250/372; 250/560
[58] Field of Search ................. 250/302, 358.1, 359.1, 250/360.1, 361 R, 365, 372, 560

[56] References Cited

U.S. PATENT DOCUMENTS 2,989,690 6/1961 Cook .................................... 250/560
3,559,253 2/1971 Pondell et al. ...................... 250/372

Primary Examiner—Bruce C. Anderson
Attorney, Agent, or Firm—Flynn, Thiel, Boutell & Tanis,

[57] ABSTRACT

A tensile tester especially useful for colored specimens having pairs of projector-optic arrangements for detecting the presence of bench marks on a specimen and each including an ultraviolet lamp projector and an optic arrangement incorporating a detector for receiving luminescent rays emitted by the bench marks on the specimen upon being irradiated ultraviolet light from the projector. Support structure and a drive arrangement are provided for causing the projector optic arrangements to pursue automatically the bench marks controlled by detection of luminescent rays by means of the detectors in the optic arrangements. Elongation detectors are provided for transmitting respective displacement signals of the arrangements in response to the operation of the support and drive arrangements. An arithmetic unit of elongation is provided differences for receiving the signals from the elongation detectors and indicating the difference in spacing between the bench marks.

5 Claims, 3 Drawing Figures

TENSILE TESTER

FIELD OF THE INVENTION

This invention relates to a tensile tester and more particularly, to a tensile tester provided with an apparatus capable of measuring elongations of a wide variety of specimens in non-contact manner and with high accuracy by irradiating the bench marks on a specimen previously marked with the aid of an ultraviolet lamp to cause emission of only the bench marks and detecting the luminescent light rays thus emitted.

BACKGROUND OF THE INVENTION

As a measurement method of elongations of a specimen, there are heretofore known, for example, a direct measurement method in which a testing person reads directly elongations of a specimen by applying a scale to it; a non-contact measurement method for which visible rays are used; a contact measurement method in which a specimen is attached with a jig for elongation measurement to determine the elongations from displacement magnitudes of the jig; etc.

The direct measurement method, however, is not suited for high accuracy measurement since the length between the bench marks moving every moment is pursued with the unaided eyes. The non-contact method with the aid of visible rays, when applied to a wide variety of colored specimens having a large elongation such as plastics or rubbers, has encountered a problem in which the texture of a specimen is discolored as the elongation of it increases and the contrast between the texture and the bench marks is changed. Accordingly, the method is defective in that elongations of all the specimens cannot always be measured accurately. For instance, the case of a black specimen will be referred to. When the black specimen is marked with white bench marks thereon and drawn, the black specimen is discolored to such a white hue that cannot be distinguished from the white color of the bench marks. When the black specimen is marked with bench marks of a red series color and drawn, before drawing the red color of the bench marks is brighter than the black color of the specimen, but as the specimen is drawn under load, it becomes discolored to a white hue brigher than the red series color of the bench marks and the brightness of the specimen is thus inverted. As a consequence, the detection of the bench marks is not feasible. Further, visible rays from the projector are reflected by the discolored white hue portion of the specimen and are incident upon the optic, so that the detection of the bench marks is more impossible. For the reasons above, it is impossible to use visible rays of the measurement of elongations of a wide variety of specimens and all colored specimens.

The contact measurement method is disadvantageous in that it is troublesome to mount the jig for elongation measurement on the specimen whenever it is measured, and in that the weight of the jig may often be responsible for causing errors. In particular, in the case of a specimen such as a film which is susceptible to breakdown even under a slight tensile load, a further drawback is seen in the fact that a load is imposed on the portion of the specimen to which the jig is attached, from where the specimen is broken down, so that it is not possible to measure elongations.

Any of the prior art measurement methods have thus many problems and drawbacks to be solved and improved for the measurement of elongations with high accuracy and precision.

With a view to coping with the prior art situation as described above, this invention is designed for measuring elongations of a wide variety of colored specimens which it has been heretofore difficult to measure by any method regardless of the non-contact method and the contact method, with high accuracy.

Therefore, an essential object of this invention is to provide a tensile tester intended for a non-contact method having an improved measurement apparatus by adopting an ultraviolet lamp as a light source of a projector.

SUMMARY OF THE INVENTION

As essential feature of this invention resides in a tensile tester comprising at least two pairs of projector-and-optic arrangements provided at an interval in the elongation direction of a specimen and each pair comprising a projector whose light source is an ultraviolet lamp and an optic incorporating a detector for receiving luminescent light rays emitted on a specimen when irradiated from the projector and for detecting the amount of the incident light upon the detector; pursuit mechanisms for permitting the projector-optic arrangements to pursue automatically bench marks on the specimen marked in its elongation direction with a fluorescent coating, with the detection by means of the detectors of the optics; elongation detectors for the projector-optic arrangements for transmitting displacement signals of the projector-optic arrangements displaced in accordance with the operation of the pursuit mechanisms; and an arithmetic unit for operation of elongation differences for receiving the transmitting signals from the elongation detectors and for operating the difference between them.

In the method of measurement on the tensile tester according to this invention, only the bench marks on a specimen marked with a fluorescent coating are brought into emission by the irradiation of ultraviolet rays.

The effect due to the reflective rays of ultraviolet rays by the white discolored portion of a specimen when loaded and drawn can be precluded by attaching a filter to the optic.

Thus, the incident light upon the detector is only of the luminescent light due to emission of the bench marks, so that according to the tester of this invention, it is possible to measure a wide variety of colored specimens with high accuracy.

The tensile tester of this invention will be hereinafter described in detail with specific embodiments thereof with reference to the accompanying drawings.

DETAILED DESCRIPTION

Figure 1:
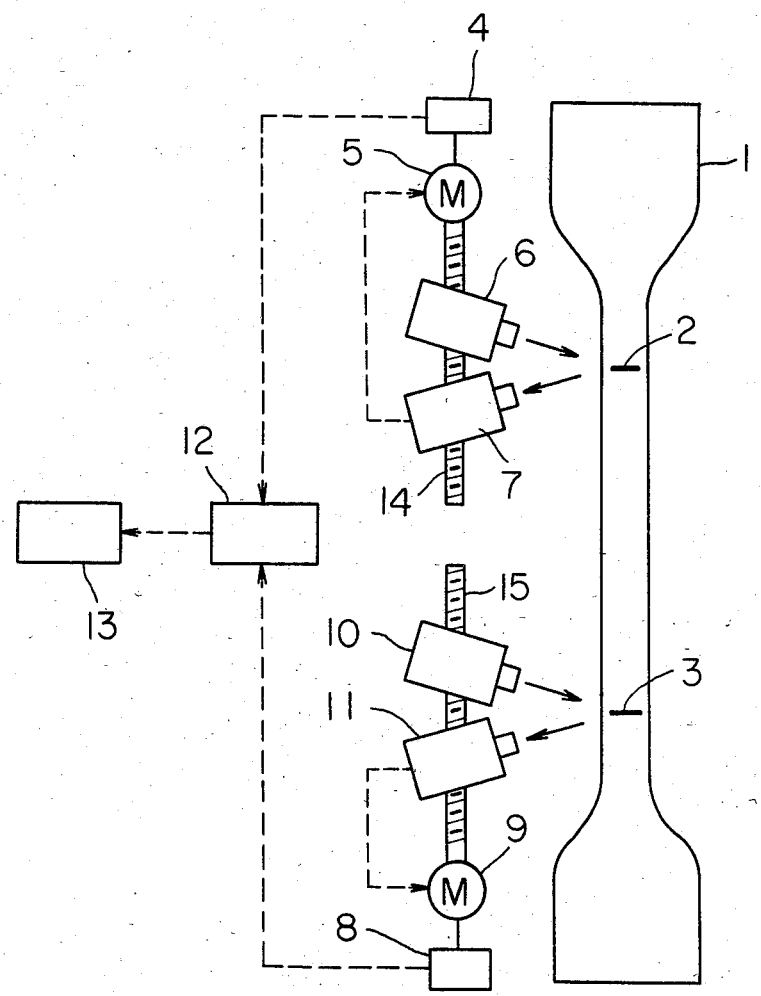
FIG. 1 is a diagrammatic representation showing one embodiment of a tesile tester of this invention.

In FIG. 1, there are shown projectors 6, 10 for irradiating ultraviolet rays to bench marks 2, 3 on a specimen 1 marked with a fluorescent coating and optics 7, 11 for receiving and detecting luminescent light rays which the specimen emits upon receiving the radiations from the projectors 6, 10. These projectors and optics constitute two sets of arrangements of projector-optic 6, 7 and 10, 11, which are disposed so as to correspond to the positions of the bench marks 2, 3 on the specimen marked at an interval in the elongation direction of it, thus constituting a fundamental element of the tensile tester.

Both the projector-optic arrangements 6,7 and 10,11 are mounted on screws 14, 15 which are actuated to revolve by the rotation of the output shafts of balancing electric motors 5, 9, which rotation is caused according to the detection of detectors (which will be described below) incorporated in the optics 7, 11, whereby the respective projector-optic arrangements 6,7 and 10,11 can pursue automatically the bench marks 2, 3 by detecting the amount of the incident light upon the optics 7, 11.

The reference numerals 4, 8 are elongation detectors for transmitting the displacements of the projector-optic arrangements 6,7 and 10,11 displaced in response to the rotation of the balancing electric motors 5, 9. Displacement signals are produced by the detectors 4, 8.

The elongation detectors 4, 8 are located at the diametrically opposite ends of the balancing electric motors 5, 9 and serve to input the respective transmission signals from the arrangements to an arithmetic unit 12 for operation of elongation differences, where operation results are recorded on a recorder 13, if required.

The essential features of the tensile tester of this invention resides in the respective constitutions as described above, and of particular importance is the constitution of the arrangements comprised of the projectors 6, 10 whose light source is an ultraviolet lamp and the optics 7, 11 paired with them.

Figure 2:
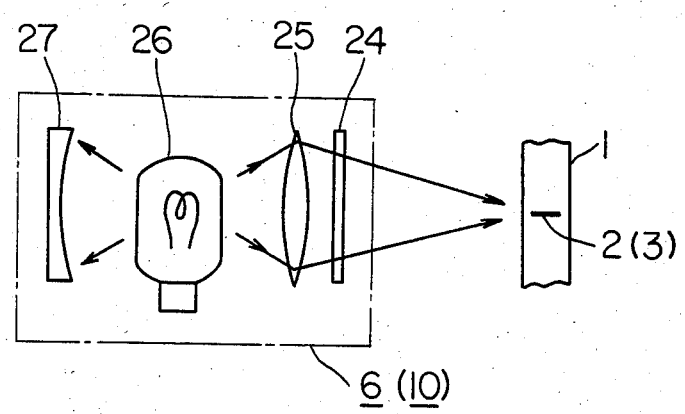
FIG. 2 is an illustration showing a constitution of the projector as shown in FIG. 1.
Figure 3:
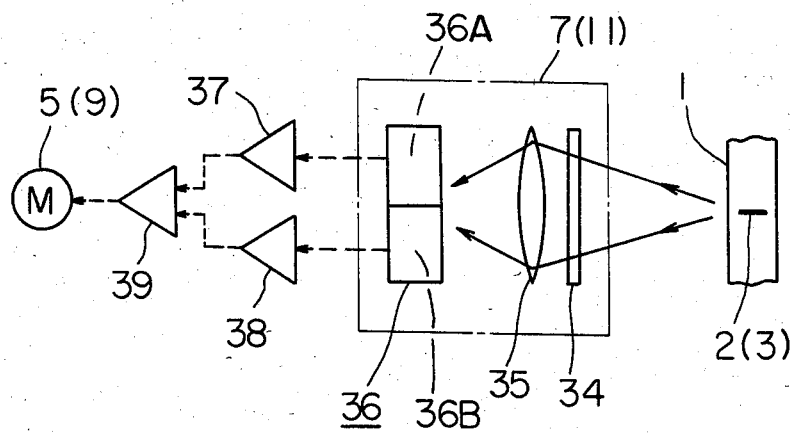
FIG. 3 is an illustration showing a constitution of the optic as shown in FIG. 1.

FIG. 2 and FIG. 3 illustrate the particulars of the projectors 6, 10 and the optics 7, 11 by which the invention is featured.

The projectors 6, 10 are each provided, as shown in FIG. 2, with an ultraviolet lamp 26, a combination of a concave mirror 27 and a convex lens 25 which serves to irradiate efficiently the emission light rays from the lamp 26 upon the bench marks 2, 3 on the specimen 1 and a light filter 24 for intercepting and removing the visible rays from the ultraviolet lamp 26 thereby cause the bench marks 2, 3 to be irradiated only with the ultraviolet rays. Thus, the effect due to the reflection from the specimen 1 which comes into a problem when visible rays are irradiated is precluded.

The optics 7, 11 are, as shown in FIG. 3, each equipped with a filter 34 for removing the ultraviolet rays when receiving the luminescent rays emitted by the bench marks 2, 3 on the specimen 1, a convex lens 35 for condensing or focusing the visible rays from which the ultraviolet rays are removed and a multi-element semiconductor detector 36 for detecting the amount of the incident light thus condensed or focused thereon. In this way the optics are constructed so as to condense only the visible rays on the convex lens 35 and to introduce them into the detector 36, whereby their reliability as a device is ensured.

In the setup of the optics 7, 11 as illustrated, the multi-element semiconductor detector 36 assumes the form of two multi-element semiconductor detectors 36A, 36B in which the multi-element is equally divided into two parts. And a mechanism is adopted in which the outputs of the multi-element semiconductor detectors 36A, 36B are amplified by respective amplifiers 37, 38 and then input to a differential amplifier 39 for amplification, and the amplified output in turn activates the balancing electric motors 5, 9 to cause the output shafts to rotate.

In this mechanism, if the optics 7, 11 and the bench marks 2, 3 correspond to each other, the outputs of the bisected multi-element semiconductor detectors 36A, 36B of the multi-element semiconductor detector 36 are equal and the output of the differential amplifier 39 is zero. Consequently, the balancing electric motors 5, 9 are in a standstill state.

Conversely, if there exists a deviation in the corresponsence between the bench marks 2, 3 and the optics 7, 11, the outputs of the equally divided multi-element semiconductor detectors 36A, 36B are differentiated and the balancing electric motors 5, 9 continue to operate until the difference between the outputs becomes zero, which operation continues to enable the pairs of the projector-optic arrangements to be displaced and to perpetually pursue automatically and precisely the targets of the bench marks 2, 3.

The construction of the tensile tester of this invention has been thus far described, and now the operation thereof will be described. In measuring elongations of a specimen, the two bench marks 2, 3 marked on the specimen 1 as shown in FIG. 1 are first irradiated with ultraviolet rays from the projectors 6, 10 and only the bench marks are caused to emit luminescent lights. The luminescent lights thus emitted are received on the optics 7, 11. The respective beams of the luminescent lights of the bench marks are passed through the filters 34 housed in the optics (Cf. FIG. 3), through which the ultraviolet rays are absorbed and removed, and only the resulting visible rays are condensed on the convex lens 35 and introduced into the multi-element semiconductor detectors 36. The respective visible rays are detected with the detectors 36 to transmit analogue signals which, after undergoing amplification action in the optics, actuate to rotate the output shafts of the balancing electric motors 5, 9.

Activation of the balancing electric motors 5, 9, on the one hand, rotates the screws 14, 15 cause movement of the projector-optic arrangements 6,7 and 10, 11 and causes them to continually pursue the positions of the bench marks 2,3 and to be displaced until an equilibrium condition is reached. On the oher hand, activation of the electric motors brings the elongation detectors 4, 8 provided at the diametrically opposite ends of the balancing electric motors 5, 9 into operation, and causes to transmit the displacement signals of the arrangements of the projector and optic into the arithmetic unit 12 for determination of the elongation differences.

When both the transmission signals from the elongation detectors 4, 8 are introduced in this way, the difference between both signals is obtained by operation of the arithmetic unit 12 to provide the elongation differences. Consequently, elongations between both bench marks 2, 3 can be automatically measured.

Thus, the tensile tester of this invention enables are to measure elongations of specimens with high accuracy by virtue of the combination of the ultraviolet projector and optic arrangement as well as the detector as well as and further mechanical driving elements therefor.

The above description has been made of the embodiment in which two pairs of arrangements of the projector and optic are provided, but any variations and modifications may be made depending on the number of bench marks. For instance, a variation may be made in which the pair number of the projector-optic arrangements is increased with the increase of the number in the bench marks, thereby permitting to measure a plurality of elongations between bench marks at the same time.

As described above, the tensile test according to the tensile tester of this invention is conducted by using a ultraviolet lamp as a light source for of the projector, submitting only the bench marks on a specimen beforehand marked to emission, detecting the luminescent light rays thus emitted with the detectors, causing the arrangements of paired projector and optic to pursue the bench marks following the detection, and measuring the elongations between the bench marks by the provision of the elongation detectors and the arithmetic unit. As a consequence, the pursuit mechanisms enable the projector-optic arrangements to perpetually pursue automatically with high accuracy the targets of the bench marks. Further, even when the tensile tester is applied to such specimens that have heretofore been difficult to measure by either the non-contact method or contact method, such as a wide variety of colored specimens having a large elongation, e.g. plastics or rubber, or specimens susceptible to discoloration in their texture when elongated, it is possible to measure elongations with very good accuracy. In addition, there are no inconveniences experienced when mounting a jig on a specimen and accordingly, causes of errors can be minimized. Hence, this invention is very useful and efficient in enhancing the automation of the measurement.

The embodiments of the invention in which an exclusive property or privilege is claimed are defined as follows:

1. A tensile tester for use in detecting the amount of elongation in a stationary specimen marked with at least a pair of fluorescent coating bench marks comprising at least two pairs of projector-optic arrangements spaced along the length of and in the elongation direction of said specimen, each pair of projector-optic arrangements comprising an ultraviolet lamp projector means for irradiating ultraviolet light onto the respective one of said bench marks and optic means including a detector means for detecting luminescent light rays reflected from the respective one of said ultraviolet light irradiated bench marks on said specimen caused by irradiation from said projector means, said detecting means measuring the amount of incident light from said bench mark;

support metans for independently supporting each of said projector-optic arrangement for movement back and forth along the length of at least a portion of said specimen adjacent a respective one of said bench marks;

drive means for independently driving said projector-optic arrangement along said portion of said specimen;

elongation detector means for each said projector-optic arrangements for transmitting respective displacement signals indicative of the amount of movement of said projector-optic arrangements; and control means for independently deactivating said drive means for stopping the movement of each said projector-optic arrangement when said detector means in said optic means detects said luminescent light rays from a respective one of said bench marks; and difference determining means responsive to both of said elongation detector means for determining and indicating the spacing between said bench marks.

2. A tensile tester as claimed in claim 1 in which said detector means in said optic means is a multi-element semiconductor detector and includes a filter for passing only luminescent light rays to said semiconductor detector.

3. A tensile tester as claimed in claim 2 in which said multi-element semiconductor detector incorporated in each said optic means consists of an equally divided multi-element semiconductor.

4. A tensile tester as claimed in claim 1 in which said drive means each comprise a balancing electric motor having a rotatable output shaft connected to a screw, said support means being mounted on said screw and movable along the length thereon in response to a rotation of said screw.

5. A tensile tester as claimed in claim 1 in which said difference determining means includes a recorder for recording the indicated spacing between said bench marks.

* * * * *